United States Patent
Saito et al.

(10) Patent No.: US 8,513,654 B2
(45) Date of Patent: Aug. 20, 2013

(54) COMPOUND FOR ORGANIC THIN-FILM TRANSISTOR AND ORGANIC THIN-FILM TRANSISTOR USING THE COMPOUND

(75) Inventors: Masatoshi Saito, Sodegaura (JP); Yuki Nakano, Sodegaura (JP); Hiroaki Nakamura, Sodegaura (JP)

(73) Assignee: Idemitsu Kosan Co. Ltd., Tokyo (JP)

( * ) Notice: Subject to any disclaimer, the term of this patent is extended or adjusted under 35 U.S.C. 154(b) by 396 days.

(21) Appl. No.: 12/936,945

(22) PCT Filed: Apr. 2, 2009

(86) PCT No.: PCT/JP2009/056855
§ 371 (c)(1),
(2), (4) Date: Oct. 8, 2010

(87) PCT Pub. No.: WO2009/125705
PCT Pub. Date: Oct. 15, 2009

(65) Prior Publication Data
US 2011/0031488 A1    Feb. 10, 2011

(30) Foreign Application Priority Data
Apr. 10, 2008    (JP) ................... 2008-102495

(51) Int. Cl.
*H01L 35/24*    (2006.01)
(52) U.S. Cl.
USPC ..................... 257/40; 257/E51.001
(58) Field of Classification Search
USPC .......................... 257/40, E51.001
See application file for complete search history.

(56) References Cited

U.S. PATENT DOCUMENTS
7,800,103 B2    9/2010    Katakura et al.
2008/0116452 A1    5/2008    Jeong et al.

FOREIGN PATENT DOCUMENTS
| CN | 1821193 | 8/2006 |
|---|---|---|
| JP | 2000 231987 | 8/2000 |
| JP | 2004 107257 | 4/2004 |
| JP | 2007 158062 | 6/2007 |
| WO | WO-2006 059486 | 6/2006 |
| WO | WO-2007 068618 | 6/2007 |
| WO | WO-2007 105473 | 9/2007 |

OTHER PUBLICATIONS

Quesada et al, "Synthesis and Fluorescence Properties of Novel Transmembrane Probes and Determination of Their Orientation within Vesicles," Helvetica Chimica Acta, vol. 83, 2000, pp. 2464-2476.*

Chuangchun Inst of Applied CHE, "Series soluble oligomer using 9,10-diacetylenic anthracene as structural unit and preparing method," Data supplied by the espacenet database—worldwide, Publication Date: Aug. 23, 2006; English Abstract of CN1821193.

(Continued)

*Primary Examiner* — Anthony Ho
(74) *Attorney, Agent, or Firm* — Millen, White, Zelano & Branigan, P.C.

(57) ABSTRACT

A compound for an organic thin film transistor having a structure shown by the following formula (1):

$$X^1\text{-L-Ar-L-}X^2 \qquad (1)$$

wherein L is —C≡C—, or —CH═CH— in a trans configuration, $X^1$ and $X^2$ are independently an alkyl group having 2 to 30 carbon atoms or a haloalkyl group having 1 to 30 carbon atoms, and Ar is a substituted or unsubstituted aromatic hydrocarbon group having 14 to 60 ring carbon atoms which is a condensed ring of three or more rings, or a substituted or unsubstituted aromatic heterocyclic group having 11 to 60 ring atoms which is a condensed ring of three or more rings.

21 Claims, 2 Drawing Sheets

(56) References Cited

OTHER PUBLICATIONS

Ebata et al., "Highly Soluble [1]Benzothieno [3,2-b]benzothiophene (BTBT) Derivatives for High-Performance, Solution-Processed Organic Field-Effect Transistors," JACS Communication, 2007, vol. 129, pp. 15732-157333.
Fujitsu Ltd., "Organic electroluminescent element and display device using it," Patent Abstracts of Japan, Publication Date: Aug. 22, 2000; English Abstract of JP 2000 231987.
International Search Report for PCT/JP2009/056855 dated May 19, 2009.
Kang, J. et al., "Synthesis of $AB_2$-Functionalized Triphenylene Derivatives," Letters in Organic Chemistry, 2006, vol. 3, pp. 674-678.
Konica Minolta Holdings Inc., "Organic Semiconductor Material, Film and Device, and Organic Thin Film Transistor," Patent Abstracts of Japan, Publication Date: Jun. 21, 2007; English Abstract of JP-2007 158062.
Konica Minolta Holdings Inc., "Organic semiconductor material, organic semiconductor film, organic semiconductor device, and organic thin film transistors," Data Supplied from the espacenet database—worldwide, Publication Date: Sep. 20, 2007; English Abstact of WO 2007 105473.
Maeda, H. et al., "Alkynylpyrenes as Improved Pyrene-Based Biomolecular Probes with the Advantages of High Fluorescene Quantum Yields and Long Absorption/Emission Wavelengths," Chemistry: A European Journal, 2006, vol. 12, pp. 824-831.
Nippon Hoso Kyokai, "Organic compound, organic thin film device and display using the same," Patent Abstract of Japan, Publication Date: Apr. 8, 2004, English Abstract of JP-2004 107257.
Rego, J. A. et al., "Synthesis of novel mixed tail triphenylene discotic liquid crystals—the search for higher order," Chemical Communications, 1996, pp. 1031-1032.
Stulgies, B. et al., "Six- and Eight-fold Palladium-Catalyzed Cross-Coupling Reactions of Hexa- and Octabromoarenes," Chemistry: A European Journal, 2005, vol. 11, pp. 306-320.
Tamai, T. et al., "Fluorescent Polymer Particles Incorporating Pyrene Derivatives," Journal of Polymer Science: Part A: Polymer Chemistry, 2008, vol. 46, pp. 1470-1475.
Walter, D. et al., "Quantum interference in polycyclic hydrocarbon molecular wires," Chemical Physics, 2004, vol. 299, pp. 139-145.
Wang, Y. et al., "Synthesis, characterization, and reactions of 6,13-distributed 2,3,9,10-tetrakis(trimethylsilyl)pentacene derivatives," Tetrahedron, 2007, vol. 63, pp. 8586-8597.

\* cited by examiner

COMPOUND FOR ORGANIC THIN-FILM TRANSISTOR AND ORGANIC THIN-FILM TRANSISTOR USING THE COMPOUND

TECHNICAL FIELD

The invention relates to a compound suited to a coating process, a compound for an organic thin film transistor and an organic thin film transistor using the compound in an organic semiconductor layer.

BACKGROUND ART

Thin film transistors (TFTs) are widely used as a switching element for a display such as a liquid crystal display device. The representative TFT has a gate electrode, an insulating layer and an organic semiconductor layer on a substrate sequentially and has a source electrode and a drain electrode formed on the organic semiconductor layer with a predetermined distance. The organic semiconductor layer forms a channel region, and an electric current flowing between the source electrode and the drain electrode is controlled by applying a voltage to the gate electrode to allow the on/off action.

Heretofore, the TFT has been made of amorphous silicon or polycrystalline silicon. However, a CVD apparatus which is used for production of the TFT using such silicon is very expensive, and to enlarge a display apparatus or the like using TFTs had a problem of significant increase in the production costs. Further, the process of making the amorphous or polycrystalline silicon into a film is carried out at a very high temperature so that materials usable for a substrate are limited. Thus, there is a problem that a lightweight substrate such as a resin substrate cannot be used.

In order to solve the problems, a TFT using an organic substance (hereinafter often referred to as an "organic TFT") in place of the amorphous or polycrystalline silicon has been proposed. As a film-forming methods used for production of a TFT with an organic substance, vacuum deposition, a coating method and the like are known. By the use of these film-forming methods, enlarging a device is feasible while suppressing an increase in production cost. Further, the process temperature required at the time of film-forming can be kept to relatively low temperature. By this, the organic TFT has an advantage of small limitation in the selection of materials used for a substrate. Therefore, practical application of the organic TFT is expected, and extensive studies and reports are made.

As materials for a p-type FET (field effect transistor) of an organic semiconductor used for an organic TFT, polymers such as conjugated polymers and thiophene polymers, metal phthalocyanine compounds, fused aromatic hydrocarbons such as pentacene, and the like are used alone or in a mixture with other compounds. As materials for an n-type FET, for example, 1,4,5,8-naphthalenetetracarboxyl dianhydride (NTCDA), 11,11,12,12-tetracyanonaphtho-2,6-quinodimethane (TCNNQD), 1,4,5,8-naphthalenetetracarboxyldiimide (NTCDI) and fluorinated phthalocyanine are known.

On the other hand, as a device using electric conduction in the same manner, an organic electroluminescence (EL) device is known. In the organic EL device, a strong electric field of $10^5$ V/cm or higher is applied to a very thin film typically having a thickness of 100 nm or less in the film thickness direction to compulsorily flow charges. On the other hand, in the case of the organic TFT, it is necessary to flow charges over distance of several μm or more at a high velocity in an electric field of $10^5$ V/cm or lower. Therefore, the organic substance itself used for an organic TFT needs to have a higher conductivity. However, the above-mentioned conventional compounds used for an organic TFT have a small field effect mobility and slow response speed, thus, they have a problem that a high response speed required in a transistor cannot be obtained. Also, the on/off ratios thereof are small.

Here, the "on/off ratio" means a value obtained by dividing an electric current flowing between the source-drain when applying a gate voltage (on) by an electric current flowing between the source-drain when applying no gate voltage (off). The "on" current usually means an electric current value (saturated electric current) at the time when an electric current flowing between the source-drain reaches saturation with a gradual increase of the gate voltage.

As the representative examples of fused aromatic hydrocarbons in the field of electronic materials, anthracene can be given. Non-Patent Document 1 discloses an organic TFT fabricated by using a single crystal of anthracene, and states that this TFT has a field effect mobility of about 0.02 cm²/Vs. However, since anthracene itself is low in solubility and boiling point (sublimation point), it is not suited to a process such as deposition and coating which are normally used in the fabrication of a TFT.

In an organic TFT, a compound which is crystalline but has a high solubility is required. In particular, no organic TFT has heretofore been fabricated using analogues of anthracene such as one having an anthracene ring alone as a ring structure.

For example, a TFT is fabricated using a compound having two or more ring structures like an anthracene oligomer disclosed in Patent Document 1. This TFT is fabricated only by a deposition process since this anthracene oligomer does not have solubility.

Patent Document 1: JP-A-2004-107257
Non-Patent Document 1: Applied Physics Letters, 84, 5383 (2004)

The invention has been made in order to solve the above-mentioned problem, and an object thereof is to provide a compound for an organic thin film transistor which is suited to a coating process. Further, the invention is aimed at providing an organic thin film transistor using it as an organic semiconductor layer.

SUMMARY OF THE INVENTION

The inventors made intensive studies in order to achieve the above-mentioned objects and found that a compound shown by the following formula (1) is suited to a coating process, and preferable as the organic semiconductor layer of an organic thin film transistor. The invention has been made based on this finding.

Namely, the invention relates to a compound for an organic thin film transistor which has a structure shown by the following formula (1):

$$X^1\text{-L-Ar-L-}X^2 \quad (1)$$

In the formula (1),

L is —C≡C— or —CH=CH— in a trans configuration, $X^1$ and $X^2$ are independently an alkyl group having 2 to 30 carbon atoms or a haloalkyl group having 1 to 30 carbon atoms, and Ar is a substituted or unsubstituted aromatic hydrocarbon group having 14 to 60 carbon atoms that form a ring (hereinafter referred to as the "ring carbon atoms") which is a condensed ring of three or more rings or a substituted or unsubstituted aromatic heterocyclic group having 11 to 60 atoms that form a ring (hereinafter referred to as the "ring atoms") which is a condensed ring of three or more rings.

The invention relates to a compound in which Ar in the formula (1) has any of the following structures.

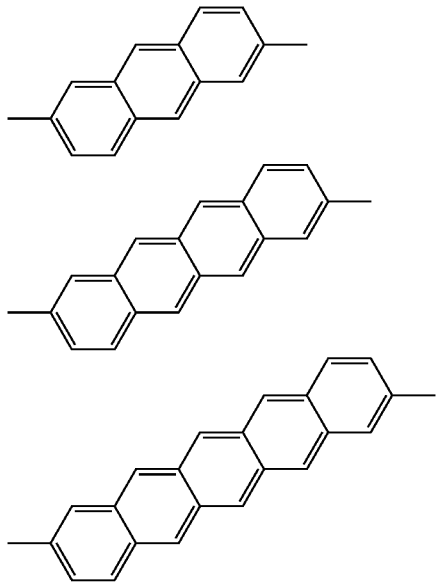

Further, the invention provides an organic thin film transistor which has three terminals of a gate electrode, a source electrode and a drain electrode, an insulating layer, and an organic semiconductor layer, and wherein a source-drain current is controlled by applying a voltage to the gate electrode, and the organic semiconductor layer comprises the organic compound having a structure shown by the formula (1).

The invention also provides an organic thin film light-emitting transistor which emits light by using current flowing between source-drain in an organic thin film transistor, and in which the light emission is controlled by applying a voltage to a gate electrode.

ADVANTAGEOUS EFFECTS OF THE INVENTION

The invention can provide a compound for an organic thin film transistor which is suited to a coating process.

By using the compound for an organic thin film transistor according to the invention as an organic semiconductor layer, an organic thin film transistor which has a high response speed (driving speed) can be provided.

The compound for an organic thin film transistor according to the invention can also be used as an organic thin film transistor which can emit light.

Figure 1:
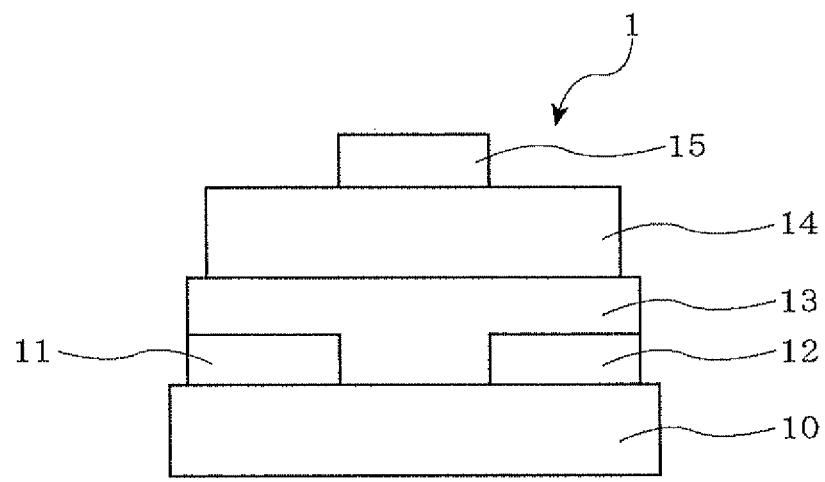
FIG. 1 is a view showing one device structure example of the organic thin film transistor device of the invention.

The compound for an organic thin film transistor of the invention has the structure shown by the following formula (1):

$$X^1\text{-L-Ar-L-}X^2 \tag{1}$$

In the formula (1), L is —C≡C— or —CH═CH— in a trans configuration. By using such a binding group which has small steric hindrance, it is possible to obtain solubility which is imparted by $X^1$ and $X^2$ while keeping the planar nature of the pi-conjugation structure shown by Ar in the formula (1). Further, by extension of the pi-conjugation structure shown by Ar to L, the molecular interaction is increased as compared with the case when Ar is alone.

In formula (1), $X^1$ and $X^2$ are independently an alkyl group having 2 to 30 carbon atoms or a haloalkyl group having 1 to 30 carbon atoms.

Examples of the alkyl group having 2 to 30 carbon atoms include an ethyl group, a propyl group, an isopropyl group, an n-butyl group, an s-butyl group, an iso-butyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosane group, an n-heneicosane group, an n-docosane group, an n-tricosane group, an n-tetracosane group, an n-pentacosane group, an n-hexacosane group, an n-heptacosane group, an n-octacosane group, an n-nonacosane group and an n-triacontane group.

Examples of the haloalkyl group having 1 to 30 carbon atoms include a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoromethyl group, a 2-fluoromethyl group, a 2-fluoroisobutyl group, a 1,2-difluoroethyl group, a difluoromethyl group, a trifluoromethyl group, a pentafluoroethyl group, a perfluorosiopropyl group, a perfluorobutyl group and a perfluorocyclohexyl group.

In the formula (1), Ar is a substituted or unsubstituted aromatic hydrocarbon group having 14 to 60 ring carbon atoms which are a condensed ring of three or more rings, or a substituted or unsubstituted aromatic heterocyclic group having 11 to 60 ring atoms which are a condensed ring of three or more rings.

Specific examples of the aromatic hydrocarbon group for Ar include residues of anthracene, tetracene, pentacene, phenanthrene, chrysene, triphenylene, corannulene, coronene, hexabenzotriphenylene, hexabenzocoronene and sumanene which may have a substituent.

Specific examples of the aromatic heterocyclic group for Ar include residues of diaza-anthracene, pyridoquinoline, pyrimidoquinazoline, pyrazinoquinoxaline, phenanthroline, carbazole, dibenzothiophene, benzodithiophene, [1]benzothieno[3,2-b]benzothiophene, dithienothiophene, dibenzofuran, benzodifuran, dithiaindenoindene, dibenzoselenophene, diselenaindenoindene and dibenzosilole which may have a substituent.

Preferably, Ar has a symmetric structure, and it is more preferable that the bonding positions thereof to two Ls be symmetric. Further, Ar preferably bonds to two Ls at such a position that pi-conjugation prolongs, since the molecules are liable to regularly orient. The examples of the partial structure of the above-mentioned —Ar— structure are given below, but the invention is not limited thereto.

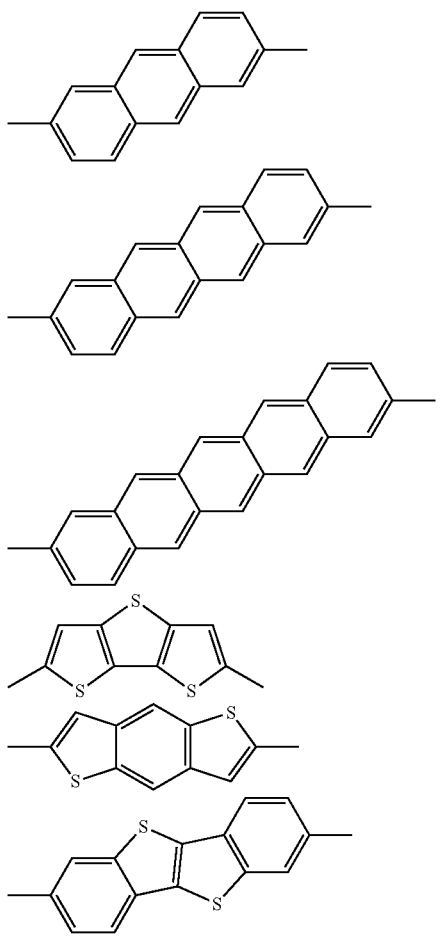

In the formula (1), the pi-conjugation of L-Ar-L preferably takes a planar structure and extends since the molecular interaction exhibits strongly. The pi-conjugation of the compound is preferably symmetric since the molecules are liable to orient regularly. Further, the entire molecule is more preferably symmetric.

The compound for an organic thin film transistor of the invention is typically a bipolar compound exhibiting p-type (hole-conducting) and n-type (electron-conducting) properties, and can be driven as a p-type element or an n-type element depending upon the combination of the source and drain electrodes explained below.

In the formula (1), by employing an electron-accepting group as a substituent which Ar may have, it is possible to decrease the level of the lowest un-occupied molecular orbital (LUMO) and to have it to function as an n-type semiconductor. Preferred electron-accepting groups include a hydrogen atom, a halogen atom, a cyano group, a haloalkyl group having 1 to 30 carbon atoms, a haloalkoxy group having 1 to 30 carbon atoms and a haloalkylsulfonyl group having 1 to 30 carbon atoms.

Also, by using an electron-donating group as the substituent which Ar may have, it is possible to increase the level of the highest occupied molecular orbital (HOMO) and to have it to function as a p-type semiconductor. Preferred electron-donating groups include a hydrogen atom, an alkyl group having 1 to 30 carbon atoms, an alkoxy group having 1 to 30 carbon atoms, an alkylamino group having 1 to 30 carbon atoms and a dialkylamino group having 2 to 60 carbon atoms (in which the amino groups may bond to each other to form a ring structure containing a nitrogen atom).

Specific examples of each group shown by the substituents which Ar in the formula (1) may have will be explained below.

The halogen atom includes fluorine, chlorine, bromine and iodine.

The alkyl group includes a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosane group, an n-henicosane group, an n-docosane group, an n-tricosane group, an n-tetracosane group, an n-pentacosane group, an n-hexacosane group, an n-heptacosane group, an n-octacosane group, an n-nonacosane group and an n-triacontane group.

The haloalkyl group includes a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-buromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoroethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group and a perfluorocyclohexyl group.

The alkoxy group is a group shown by —$OY^1$. Examples of $Y^1$ include the same groups exemplified as the alkyl groups mentioned above. The haloalkoxy group is a group shown by —$OY^2$, Examples of $Y^2$ include the same groups exemplified as the haloalkyl groups mentioned above.

The alkylthio group is a group shown by —$SY^1$. Examples of $Y^1$ include the same groups exemplified as the alkyl groups mentioned above. The haloalkylthio group is a group shown by —$SY^2$. Examples of $Y^2$ include the same groups exemplified as the haloalkyl groups mentioned above.

The alkylamino group is a group shown by —$NHY^1$. The dialkylamino group is a group shown by —$NY^1Y^3$. Examples of $Y^1$ and $Y^3$ include the same groups exemplified as the alkyl groups mentioned above, respectively. The alkyl groups of the dialkylamino group may bond to each other to form a ring structure containing a nitrogen atom. The ring structure includes pyrrolidine and piperidine.

The alkylsulfonyl group is a group shown by —$SO_2Y^1$. Examples of $Y^1$ include the same groups exemplified as the alkyl groups mentioned above. The haloalkylsulfonyl group is a group shown by —$SO_2Y^2$. Examples of $Y^2$ include the same groups exemplified as the haloalkyl groups mentioned above.

The aromatic hydrocarbon group includes a phenyl group, a naphthyl group, an anthryl group, a phenanthryl group, a fluorenyl group, a perylenyl group, a tetracenyl group and a pentacenyl group.

The aromatic heterocyclic group includes a dithienophenyl group, a benzofuranyl group, a benzothiophenyl group, a quinolinyl group, a carbazolyl group, a dibenzofuranyl group, a dibenzothiophenyl group and a benzothiadiazonyl group.

The alkylsilyl group is a group shown by $-SiY^1Y^3Y^4$. Examples of $Y^1$, $Y^3$ and $Y^4$ include the same groups exemplified as the alkyl groups mentioned above, respectively.

The alkylsilylacetylene group is a group wherein the alkylsilyl groups are combined via an ethynylene group, and examples thereof include a trimethylsilylacetylene group, a triethylsilylacetylene group and a triisopropylsilylacetylene group.

The substituents which Ar may have are preferably located on the positions not impairing the planarity of the pi-conjugated structure formed by L-Ar-L-.

As the substituents which Ar may have, a hydrogen atom, a halogen atom and a cyano group are preferable.

Substituents which may be further substituted on the substituent which each group in the formula (1) has, include an aromatic hydrocarbon group, an aromatic heterocyclic group, an alkyl group, an alkoxy group, an aryloxy group, an arylthio group, an alkoxycarbonyl group, an amino group, a halogen atom, a cyano group, a nitro group, a hydroxy group and a carboxy group.

The compound shown by the following formula (2), that is, a compound shown by the formula (1) in which Ar has one of the following Ar' structures, is a novel compound. Therefore, this compound is not limited to one for use in an organic thin film transistor, although it can be preferably used in an organic thin film transistor.

$$X^1\text{-L-Ar'-L-}X^2 \qquad (2)$$

In the formula (2), L is $-C\equiv C-$, or $-CH=CH-$ in a trans configuration, $X^1$ and $X^2$ are independently an alkyl group having 2 to 30 carbon atoms or a haloalkyl group having 1 to 30 carbon atoms, and Ar' is one of the following structures:

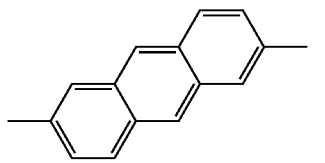

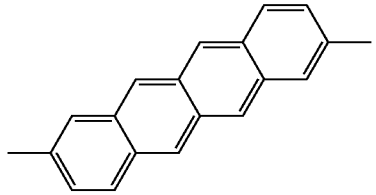

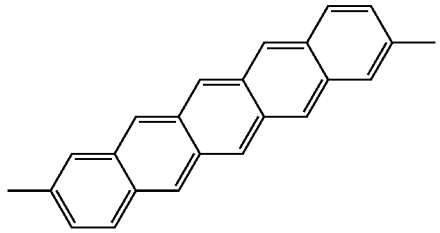

In the compound shown by the formula (1), the bonding positions between $X^1$ and L, between $X^2$ and L, and between Ar and L are preferably configured such that a pi-conjugation structure formed by $X^1$-L-Ar-L-$X^2$ has the maximum conjugated length. For instance, among the following compounds (a) and (b), the bond is preferably formed to be the structure (b).

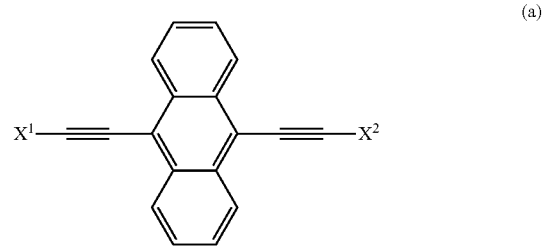

(a)

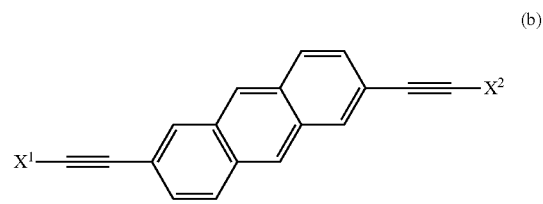

(b)

Specific examples of the compounds for an organic thin film transistor of the invention will be mentioned below. However, the invention is not limited thereto.

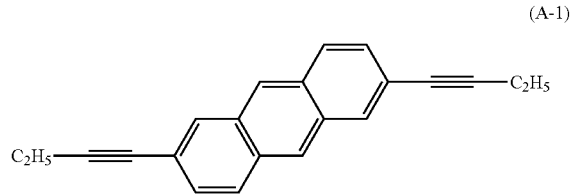

(A-1)

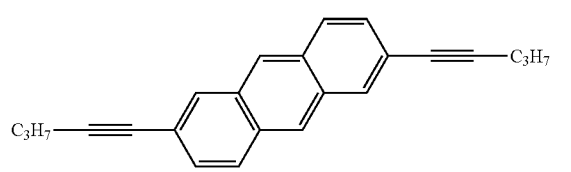

(A-2)

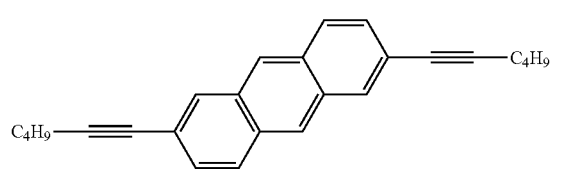

(A-3)

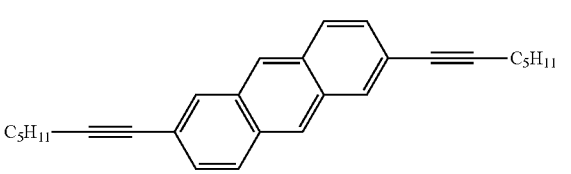

(A-4)

-continued
(A-5)
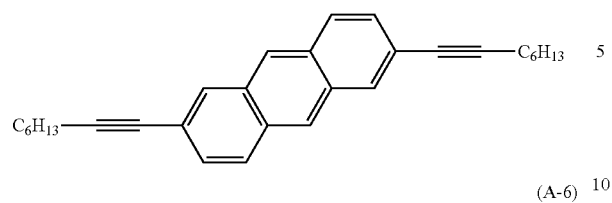
(A-6)
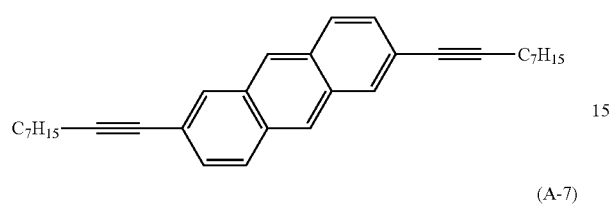
(A-7)
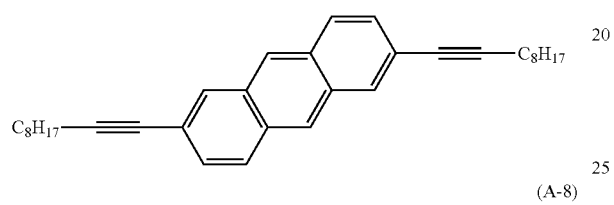
(A-8)
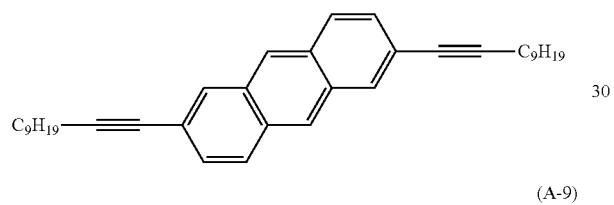
(A-9)
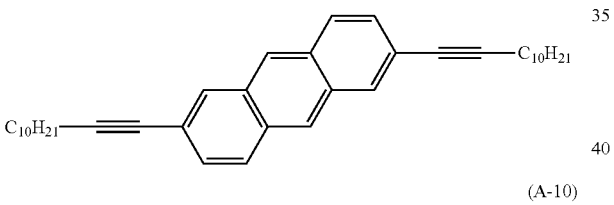
(A-10)
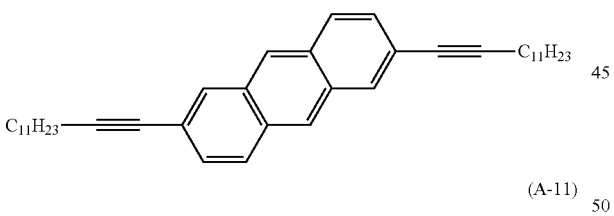
(A-11)
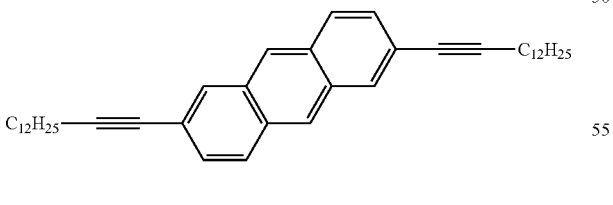
(A-12)
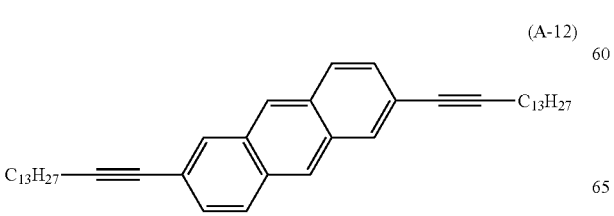
-continued
(B-1)
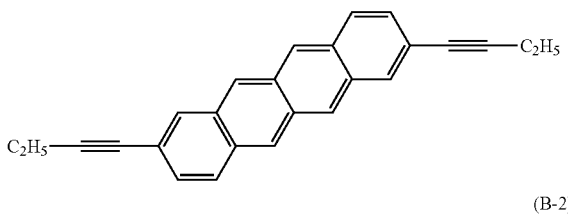
(B-2)
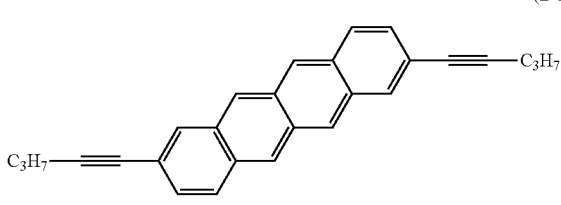
(B-3)
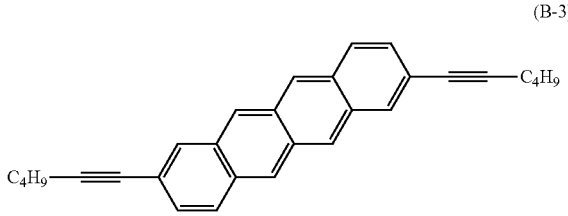
(B-4)
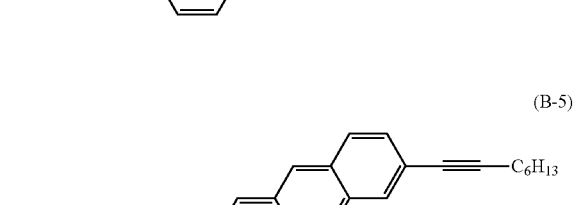
(B-5)
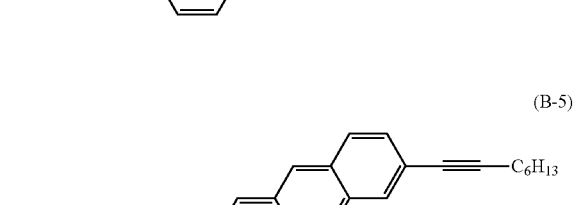
(B-6)
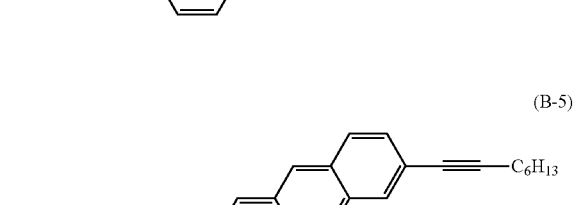
(B-7)
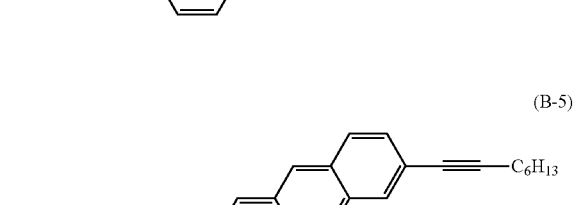

(B-8)
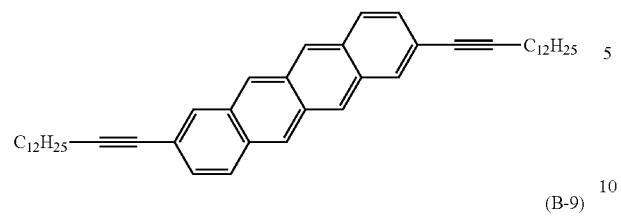
(B-9)
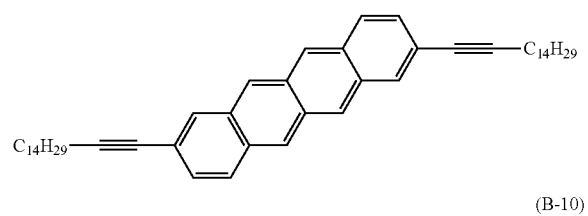
(B-10)
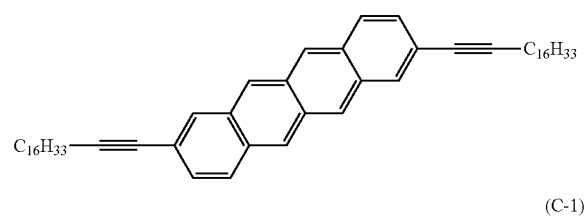
(C-1)
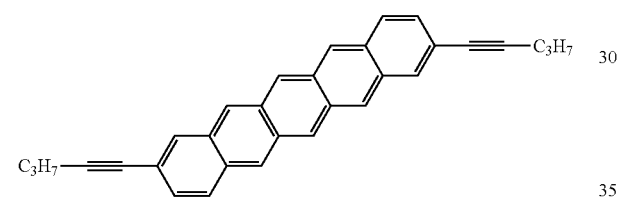
(C-2)
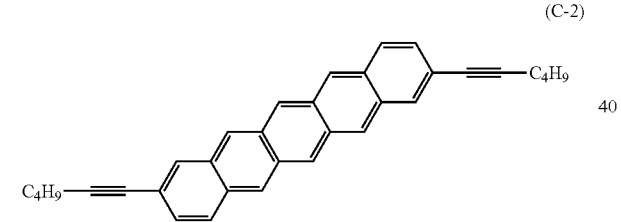
(C-3)
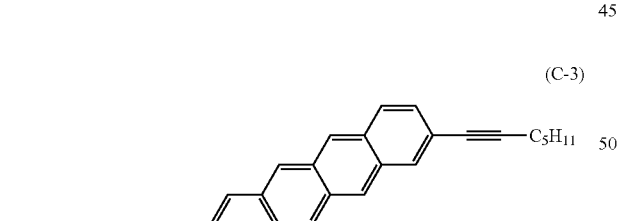
(C-4)
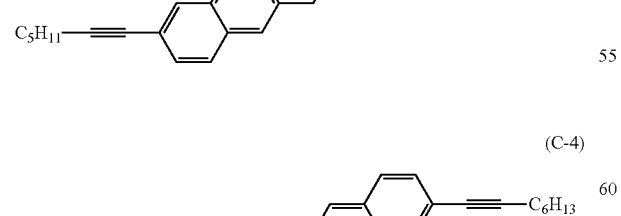
(C-5)
(C-6)
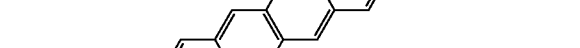
(C-7)
(C-8)
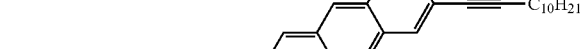
(C-9)
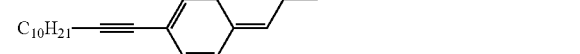
(D-1)
(D-2)
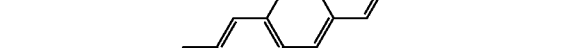

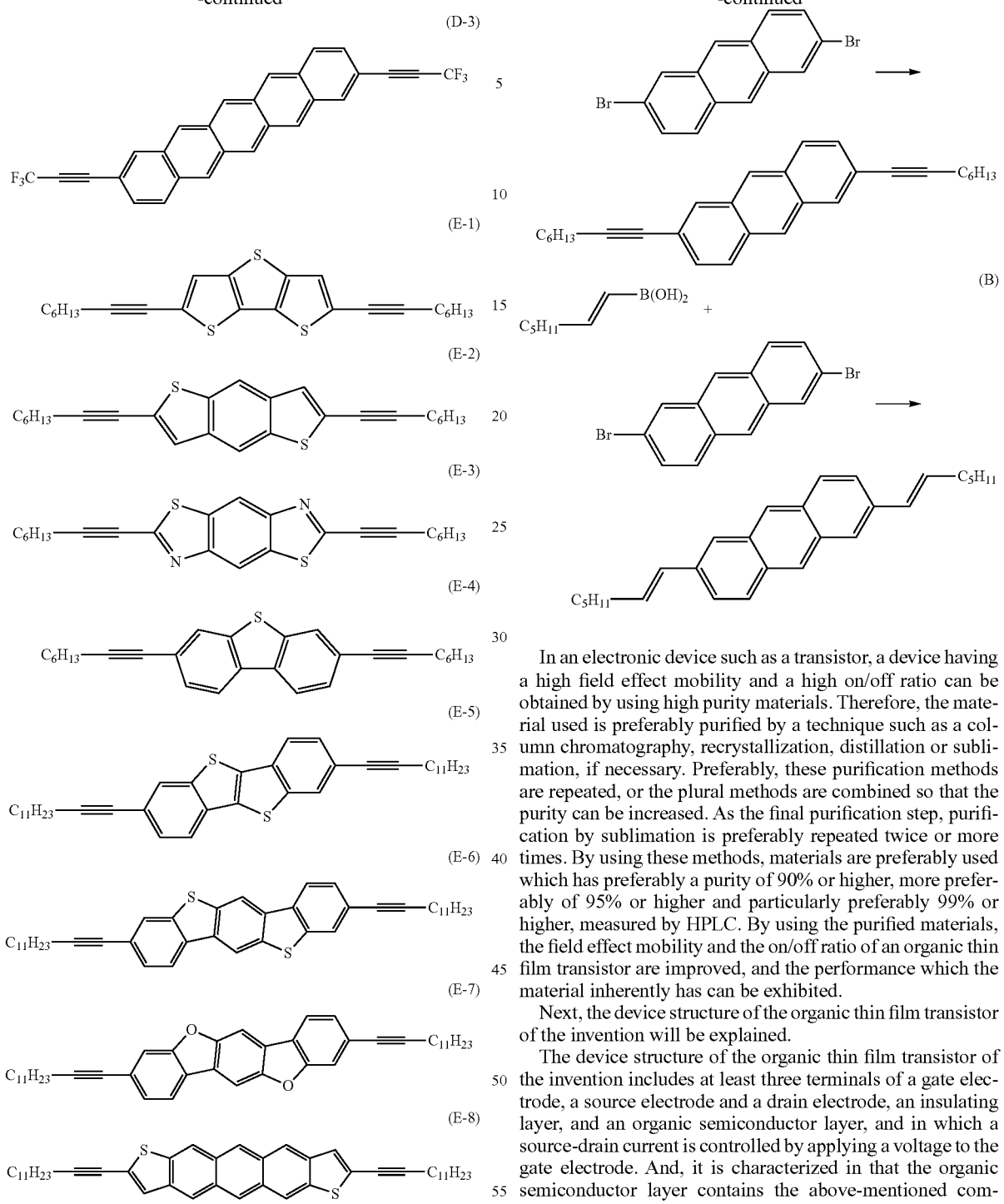

The compound for an organic thin film transistor of the invention can be synthesized by known methods such as a variety of coupling reactions using a transition metal catalyst like the following reaction (A) or (B) represented by Sonogashira coupling and Suzuki-Miyaura coupling.

(A)

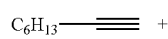   +

In an electronic device such as a transistor, a device having a high field effect mobility and a high on/off ratio can be obtained by using high purity materials. Therefore, the material used is preferably purified by a technique such as a column chromatography, recrystallization, distillation or sublimation, if necessary. Preferably, these purification methods are repeated, or the plural methods are combined so that the purity can be increased. As the final purification step, purification by sublimation is preferably repeated twice or more times. By using these methods, materials are preferably used which has preferably a purity of 90% or higher, more preferably of 95% or higher and particularly preferably 99% or higher, measured by HPLC. By using the purified materials, the field effect mobility and the on/off ratio of an organic thin film transistor are improved, and the performance which the material inherently has can be exhibited.

Next, the device structure of the organic thin film transistor of the invention will be explained.

The device structure of the organic thin film transistor of the invention includes at least three terminals of a gate electrode, a source electrode and a drain electrode, an insulating layer, and an organic semiconductor layer, and in which a source-drain current is controlled by applying a voltage to the gate electrode. And, it is characterized in that the organic semiconductor layer contains the above-mentioned compound for an organic thin film transistor of the invention. Typically, the organic thin film transistor is formed on a substrate.

The structure of the transistor is not particularly limited and may have a known device structure except the component of the organic semiconductor layer. Specific examples of the device structures of the organic thin film transistor will be explained with reference to drawings.

FIGS. 1 to 4 are views showing one example of the device structure of the organic thin film transistor of the invention.

An organic thin film transistor 1 shown by FIG. 1 has a source electrode 11 and a drain electrode 12 on a substrate 10, which are formed to be opposed to each other with a predetermined spacing. An organic semiconductor layer 13 is formed to cover the source electrode 11, the drain electrode 12 and the spacing therebetween, and an insulating layer 14 is stacked thereon. A gate electrode 15 is formed on the insulating layer 14 and above the spacing between the source electrode 11 and the drain electrode 12.

Figure 2:
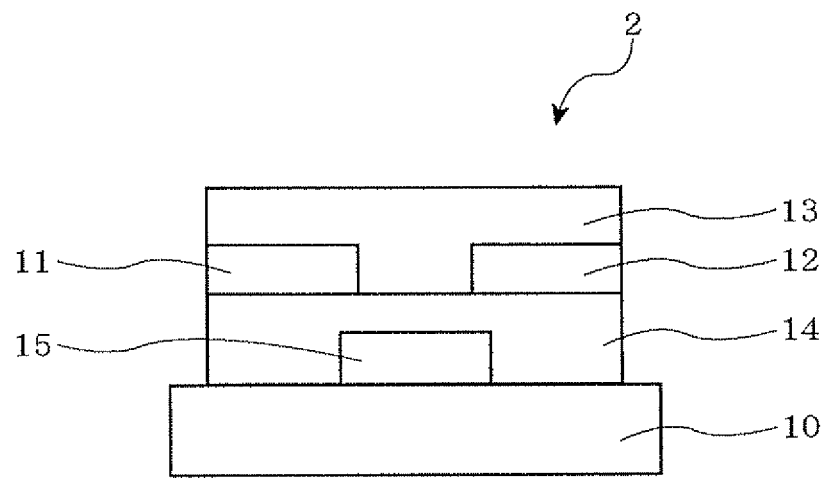
FIG. 2 is a view showing one device structure example of the organic thin film transistor device of the invention.

An organic thin film transistor 2 of FIG. 2 has a gate electrode 15 and an insulating layer 14 in sequence on a substrate 10, a pair of a source electrode 11 and a drain electrode 12 formed with a predetermined spacing on the insulating layer 14, and an organic semiconductor layer 13 is formed on the source electrode 11 and the drain electrode 12. The organic semiconductor layer 13 forms a channel region, and a current flowing between the source electrode 11 and the drain electrode 12 is controlled by a voltage applied to the gate electrode 15 so that an on/off operation is carried out.

Figure 3:
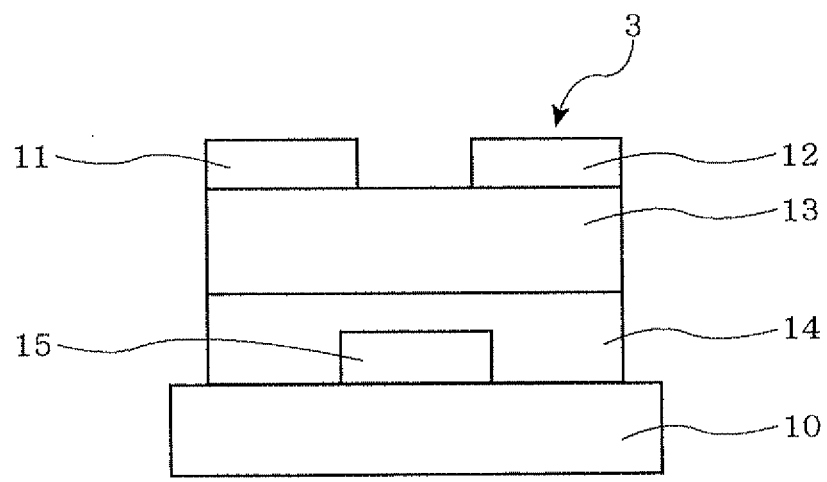
FIG. 3 is a view showing one device structure example of the organic thin film transistor device of the invention.

An organic thin film transistor 3 shown by FIG. 3 has a gate electrode 15, an insulating layer 14 and an organic semiconductor layer 13 in sequence on a substrate 10, and has a pair of a source electrode 11 and a drain electrode 12 formed with a predetermined spacing on the organic semiconductor layer 13.

Figure 4:
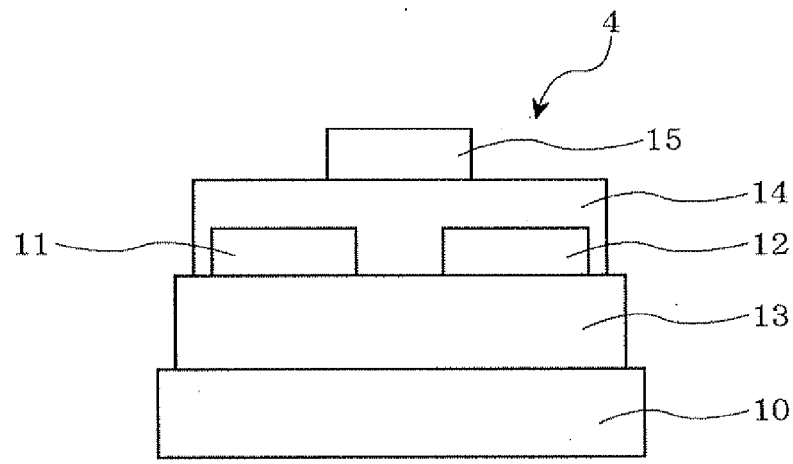
FIG. 4 is a view showing one device structure example of the organic thin film transistor device of the invention.

An organic thin film transistor 4 shown by FIG. 4 has an organic semiconductor layer 13 on a substrate 10, and has a pair of a source electrode 11 and a drain electrode 12 formed with a predetermined spacing on the organic semiconductor layer 13. Further, it has an insulating layer 14 and a gate electrode 15 in sequence.

The organic thin film transistor of the invention has a field effect transistor (FET) structure. As mentioned above, some structures are possible depending upon the position of electrodes, stacking order of layers and the like. An organic thin film transistor has an organic semiconductor layer (an organic compound layer), a source electrode and a drain electrode formed to be opposed to each other with a predetermined spacing, and a gate electrode formed with each predetermined spacing from the source electrode and the drain electrode. A current flowing between source-drain electrodes is controlled by applying a voltage to the gate electrode. Here, the spacing between the source electrode and the drain electrode is determined depending on uses of the organic thin film transistor of the invention. It is usually 0.1 μm to 1 mm, preferably 1 μm to 100 μm, and more preferably 5 μm to 100 μm.

As for the organic thin film transistor of the invention, various structures of organic thin film transistors have been proposed. It is not limited to those device structures as long as it has a structure wherein effects such as an on/off operation and amplification by controlling a current flowing between the source electrode and the drain electrode by a voltage applied to the gate electrode are exhibited.

Figure 5:
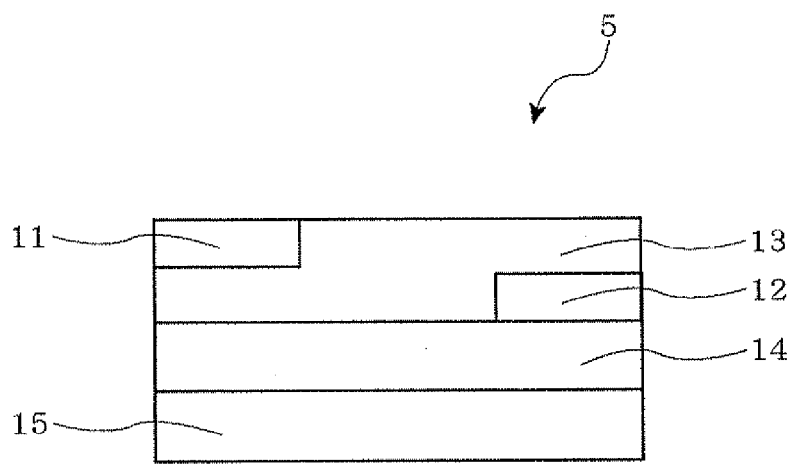
FIG. 5 is a view showing one device structure example of the organic thin film transistor device of the invention.
Figure 6:
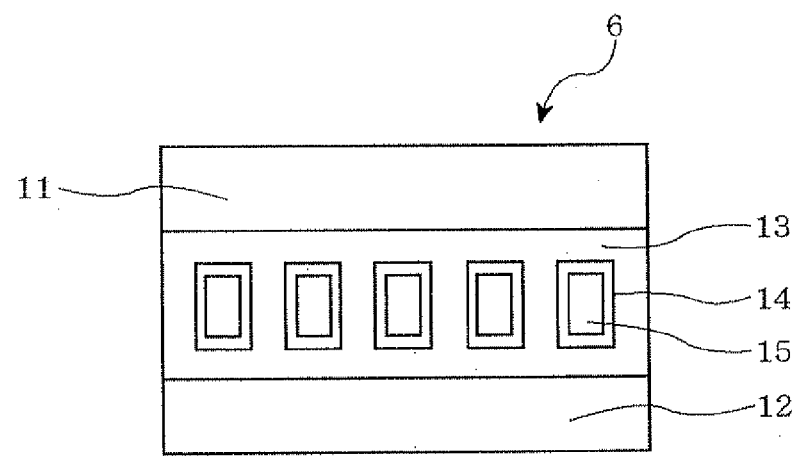
FIG. 6 is a view showing one device structure example of the organic thin film transistor device of the invention.

For instance, a top and bottom contact type organic thin film transistor proposed by Yoshida et al. of National Institute of Advanced Industrial Science and Technology in Proceedings of the 49th Meeting of The Japan Society of Applied Physics and Related Societies, 27a-M-3 (March, 2002) (see FIG. 5) and a vertical type organic thin film transistor proposed by Kudo et al. of Chiba University in Papers of Electrical Engineers of Japan, 118-A (1998), p. 1440 (see FIG. 6) may be employed.

Now, components of the organic thin film transistor will be explained below.
(Organic Semiconductor Layer)

The organic semiconductor layer in the organic thin film transistor of the invention contains the above-mentioned compound for an organic thin film transistor of the invention. The thickness of the organic semiconductor layer is not particularly limited but it is usually 0.5 nm to 1 μm, and preferably 2 nm to 250 nm.

The forming method of the organic semiconductor layer is not particularly limited, and known methods may be used. For instance, the organic semiconductor layer is formed of the above-mentioned material for an organic semiconductor layer by molecular beam epitaxy (MBE), vacuum vapor deposition, chemical deposition, printing or application method using a solution of a material dissolved in a solvent, such as a dipping method, a spin coating method, a casting method, a bar-coating method or a roll-coating method, baking, electropolymerization, self-assembly from a solution, or a combination thereof.

When crystallinity of the organic semiconductor layer is increased, the field-effect mobility is improved. Therefore, if film formation is conducted in a vapor phase (deposition, sputtering or the like), it is preferred that the substrate temperature during the film formation be kept high. This temperature is preferably 50 to 250° C., with 70 to 150° C. being further preferable. Annealing is preferably carried out after film formation irrespective of the film forming method used since a high performance device can be obtained. The annealing temperature is preferably 50 to 200° C. and more preferably 70 to 200° C. The annealing time is preferably 10 minutes to 12 hours and more preferably 1 to 10 hours.

In the invention, for the organic semiconductor layer, one kind of the compound shown by the formula (1) may be used, and plural kinds thereof may be combined. By using known semiconductors such as pentacene and a thiophene oligomer, it may be formed to a thin film in which plural materials are mixed, and plural layers formed of different materials may be stacked.
(Substrate)

The substrate of the organic thin film transistor of the invention has a function of supporting the structure of the organic thin film transistor. As the material, in addition to glass, inorganic compounds such as metal oxides and metal nitrides, plastic films (PET, PES and PC), metal substrates, composites thereof and stacked bodies thereof can be used. When the organic thin film transistor structure can sufficiently be supported by a component other than the substrate, no substrate may be used. As the material for the substrate, silicon (Si) wafer is often used. In this case, Si itself can be used as both of the gate electrode and the substrate. Further, the surface of Si may be oxidized to form $SiO_2$, which is used as an insulating layer. In this case, a metal layer such as Au may be formed on the Si substrate which is used as both the substrate and the gate electrode, as an electrode for connection with a lead wire.
(Electrode)

Materials for the gate electrode, the source electrode and the drain electrode in the organic thin film transistor of the invention are not particularly limited as long as they are electrically conductive. Platinum, gold, silver, nickel, chromium, copper, iron, tin, antimony, lead, tantalum, indium, palladium, tellurium, rhenium, iridium, aluminum, ruthenium, germanium, molybdenum, tungsten, antimony tin oxide, indium tin oxide (ITO), fluorine-doped zinc oxide, zinc, carbon, graphite, glassy carbon, silver paste, carbon paste, lithium, beryllium, sodium, magnesium, potassium, calcium, scandium, titanium, manganese, zirconium, gallium, niobium, sodium-potassium alloy, a magnesium/copper mixture, a magnesium/silver mixture, a magnesium/aluminum mixture, a magnesium/indium mixture, an aluminum/aluminum oxide mixture, a lithium/aluminum mixture and the like may be used.

Methods of forming the electrodes include deposition, electron beam deposition, sputtering, an atmospheric pressure plasma process, ion plating, chemical vapor deposition, electrodeposition, electroless plating, spin coating, printing and inkjet. As patterning methods to be used as required, a method wherein the conductive thin film formed by the above-mentioned method is subjected to known photolithography or a lift-off method to make an electrode, and a method wherein a resist film is formed on a metal foil such as aluminum or copper by thermal transfer, inkjet or the like, and etching is conducted may be mentioned.

The thickness of the electrode thus formed is not particularly limited as long as electric current can flow but it is preferably within a range of 0.2 nm to 10 μm and more preferably 4 nm to 300 nm. Within the preferable range, voltage drop would not occur due to high resistance because of the small film thickness. Further, film formation would not take long time since it is not so thick. When other layers such as a protective film and an organic semiconductor layer are stacked, bumps would not generate so that a stacked film could be smoothly obtained.

In the organic thin film transistor of the invention, as the source electrode, the drain electrode and the gate electrode, and the methods of forming them, electrodes formed from a fluid material for an electrode such as a solution, a paste, an ink and a dispersion containing the above-mentioned conductive material and particularly a fluid material for an electrode containing a conductive polymer, or metal fine particles containing platinum, gold, silver or copper are preferable. As the solvent or dispersion medium, to decrease damage to the organic semiconductor, ones which contain water in an amount of 60 mass % or more and preferably 90 mass % or more are preferable. As the dispersion containing metal fine particles, for example, a known conductive paste or the like may be used. Typically, a dispersion which contains metal fine particles having a particle diameter of 0.5 nm to 50 nm, and preferably 1 nm to 10 nm is preferable. As materials for the metal fine particles, for example, platinum, gold, silver, nickel, chromium, copper, iron, tin, antimony, lead, tantalum, indium, palladium, tellurium, rhenium, iridium, aluminum, ruthenium, germanium, molybdenum, tungsten and zinc may be used. It is preferable to form an electrode using a dispersion wherein these metal fine particles are dispersed in a dispersion liquid such as water or any organic solvent by using a dispersion stabilizer composed mainly of an organic material. The method of preparing such a dispersion of metal fine particles includes physical production methods such as a gas evaporation technique, sputtering and a metal vapor synthesis technique, and chemical production methods such as a colloid method and a coprecipitation method wherein metal ions are reduced in a liquid phase to generate metal fine particles. Preferred are dispersions of metal fine particles prepared by colloid methods disclosed in JP-A-H11-76800, JP-A-H11-80647, JP-A-H11-319538 and JP-A-2000-239853, and gas evaporation techniques disclosed in JP-A-2001-254185, JP-A-2001-53028, JP-A-2001-35255, JP-A-2000-124157 and JP-A-2000-123634.

Patterning may be conducted by a direct inkjet method using these dispersions of metal fine particles and may also be formed from a coating film by lithography, laser ablation or the like. Further, methods may be used wherein patterning is carried out by a printing method such as letterpress, intaglio printing, surface printing or screen printing. After the electrode is formed and the solvent is evaporated, heating at a temperature range of 100° C. to 300° C. and preferably 150° C. to 200° C., if necessary, is carried out in a desired shape to fusion bond the metal fine particles with heat to form an electrode pattern having a desired shape.

Further, it is preferable to use known conductive polymers having an increased electric conductivity by doping or the like as the material for the gate electrode, the source electrode and the drain electrode. For example, conductive polyanilines, conductive polypyrroles, conductive polythiophenes (complexes of polyethylenedioxythiphene and polystyrenesulfonic acid, and the like) and the like are preferably used. By these materials, contact resistance of the source electrode and the drain electrode with the organic semiconductor layer can be reduced. The electrodes may be formed and patterned by an inkjet method or may be formed from a coating film by lithography, laser ablation or the like. Further, patterning methods such as letterpress printing, intaglio printing, surface printing, screen printing and the like can be used.

Of these, the materials for forming the source electrode and the drain electrode are particularly preferably ones which have smaller electric resistance at the contact surface with the organic semiconductor layer. This electric resistance corresponds to the field effect mobility of an electric current control device to be formed. To obtain a larger mobility, it is necessary to decrease the resistance as much as possible. In general, this depends on the magnitude relation between the work function of the electrode material and the energy level of the organic semiconductor layer.

When the work function (W) of an electrode material is represented by a, the ionization potential (Ip) of an organic semiconductor layer by b, and the electron affinity (Af) of the organic semiconductor layer by c, the following relational expression is preferably satisfied. Here, all of a, b and c are positive numerical values with reference to the vacuum level.

In the case of a p-type organic thin film transistor, b−a<1.5 eV (expression (1)) is preferable, and b−a<1.0 eV is more preferable. If the above-mentioned relation with the organic semiconductor layer can be maintained, a high performance device can be obtained. However, it is preferable to select an electrode material having a work function as large as possible, the work function is preferably 4.0 eV or more, and more preferably 4.2 eV or more. Work function values of metals are described in, for example, Chemical Handbook, Basic Edition, II-493 (3rd Edition, edited by The Chemical Society of Japan, issued by Maruzen, 1983). Metals having a work function of 4.0 eV or more may be selected from the list. The metals having a high work function mainly include Ag (4.26, 4.52, 4.64, 4.74 eV), Al (4.06, 4.24, 4.41 eV), Au (5.1, 5.37, 5.47 eV), Be (4.98 eV), Bi (4.34 eV), Cd (4.08 eV), Co (5.0 eV), Cu (4.65 eV), Fe (4.5, 4.67, 4.81 eV), Ga (4.3 eV), Hg (4.4 eV), Ir (5.42, 5.76 eV), Mn (4.1 eV), Mo (4.53, 4.55, 4.95 eV), Nb (4.02, 4.36, 4.87 eV), Ni (5.04, 5.22, 5.35 eV), Os (5.93 eV), Pb (4.25 eV), Pt (5.64 eV), Pd (5.55 eV), Re (4.72 eV), Ru (4.71 eV), Sb (4.55, 4.7 eV), Sn (4.42 eV), Ta (4.0, 4.15, 4.8 eV), Ti (4.33 eV), V (4.3 eV), W (4.47, 4.63, 5.25 eV) and Zr (4.05 eV).

Of these, noble metals (Ag, Au, Cu and Pt), Ni, Co, Os, Fe, Ga, Ir, Mn, Mo, Pd, Re, Ru, V and W are preferable. In addition to metals, ITO, conductive polymers such as polyaniline and PEDOT:PSS, and carbon are preferable. Even where the electrode material contains one or plural kinds of these substances having a high work function, there is no particular limitation as long as the work function satisfies the expression (I).

In the case of an n-type organic thin film transistor, preferable is a−c<1.5 eV (formula (II)) and more preferable is a−c<1.0 eV. When the above-mentioned relationship with the organic semiconductor layer is maintained, a high performance device can be obtained. However, it is particularly preferable to select the electrode material having a work function as small as possible. The work function of the electrode material is preferably 4.3 eV or less and more preferably 3.7 eV or less.

Specific examples of metals having a low work function can be selected from the list of effective metals having a work function of 4.3 eV or less, which are described in Chemical Handbook, Basic Edition, II-493 (3rd Edition, edited by The Chemical Society of Japan, issued by Maruzen, 1983), and include Ag (4.26 eV), Al (4.06, 4.28 eV), Ba (2.52 eV), Ca (2.9 eV), Ce (2.9 eV), Cs (1.95 eV), Er (2.97 eV), Eu (2.5 eV), Gd (3.1 eV), Hf (3.9 eV), In (4.09 eV), K (2.28), La (3.5 eV), Li (2.93 eV), Mg (3.66 eV), Na (2.36 eV), Nd (3.2 eV), Rb (4.25 eV), Sc (3.5 eV), Sm (2.7 eV), Ta (4.0, 4.15 eV), Y (3.1 eV), Yb (2.6 eV) and Zn (3.63 eV). Of these, Ba, Ca, Cs, Er, Eu, Gd, Hf, K, La, Li, Mg, Na, Nd, Rb, Y, Yb and Zn are preferable. Even where the electrode material contains one or plural kinds of these substances having a low work function, there is no particular limitation as long as the work function satisfies the expression (II). However, the metals having a low work function readily deteriorate when they contact moisture or oxygen in the atmosphere. Therefore, it is desired to coat the metals with a metal stable in the atmosphere such as Ag or Au, if necessary. Necessary thickness of the coating is 10 nm or more. The larger the thickness of the coating is, the more effective the protection from oxygen and water is. However, 1 µm or less is desired in terms of usefulness and improved productivity.

In the organic thin film transistor of the invention, for example, for the purpose of increasing the injection efficiency, a buffer layer may be provided between the organic semiconductor layer, and the source electrode and the drain electrode. For an n-type organic thin film transistor, the buffer layer is preferably formed of a compound having an ion bond with an alkali metal or an alkaline earth metal such as LiF, $Li_2O$, CsF, $Na_2CO_3$, KCl, $MgF_2$ or $CaCO_3$, which is used for the cathode in an organic EL device. In addition, compounds used for the electron-injecting layer and the electron-transporting layer in an organic EL device, such as Alq may be inserted.

For a p-type organic thin film transistor, $FeCl_3$, cyano compounds such as TCNQ, $F_4$-TCNQ and HAT, oxides of metals other than alkali metals and alkaline earth metals, such as CFx, $GeO_2$, $SiO_2$, $MoO_3$, $V_2O_5$, $VO_2$, $V_2O_3$, MnO, $Mn_3O_4$, $ZrO_2$, $WO_3$, $TiO_2$, $In_2O_3$, ZnO, NiO, $HfO_2$, $Ta_2O_5$, $ReO_3$ and $PbO_2$, and inorganic compounds such as ZnS and ZnSe are preferable. In these oxides, oxygen deficiency often occurs, which suitably operates for hole-injection. Furthermore, Amine-based compounds such as TPD and NPD, and CuPc, and the like may be used which are compounds used for the hole-injecting layer and the hole-transporting layer in an organic EL device. Also, the buffer layer is desirably formed of two or more kinds of the above-mentioned compounds.

It has been known that the buffer layer has an effect to reduce the threshold voltage by decreasing the injection barrier of carriers, and to drive the transistor with a low voltage. In addition, we found that the compound of the invention has not only the effect of decreasing the voltage but also the effect of increasing the mobility. The reason therefor is as follows: There is a carrier trap at the interface of the organic semiconductor and the insulating layer. When a gate voltage is applied, injection of carries occurs. The carriers injected at the beginning are used to fill up the trap. However, when the buffer layer is provided, the trap is filled up under a low voltage so that the mobility is increased. The buffer layer may be provided between the electrode and the organic semiconductor layer with a small thickness, and the thickness is 0.1 nm to 30 nm and preferably 0.3 nm to 20 nm.

(Insulating Layer)

Materials for the insulating layer in the organic thin film transistor of the invention are not particularly limited as long as they have an electric insulation and can be made into a thin film. Materials having an electric resistance of 10 Ωcm or more at room temperature such as metal oxides (including oxides of silicon), metal nitrides (including nitrides of silicon), polymers, and organic low-molecular-weight compounds can be used. In particular, inorganic oxide films having high relative permittivity are preferable.

The inorganic oxides include silicon oxide, aluminum oxide, tantalum oxide, titanium oxide, tin oxide, vanadium oxide, barium strontium titanate, barium titanate zirconate, lead titanate zirconate, lead-lanthanum titanate, strontium titanate, barium titanate, lanthanum oxide, fluorine oxide, magnesium oxide, bismuth oxide, bismuth titanate, niobium oxide, strontium bismuth titanate, bismuth strontium tantalate, tantalum pentoxide, bismuth tantalate niobate and trioxide yttrium, and combinations thereof. Silicon oxide, aluminum oxide, tantalum oxide and titanium oxide are preferable.

Also, inorganic nitrides such as silicon nitride ($Si_3N_4$, $Si_xN_y$ (x, y>0)) and aluminum nitride are also suitably used.

Further, the insulating layer may be formed of a precursor substance containing a metal alkoxide. A solution of the precursor substance is applied on a substrate, followed by wet chemical treatment including heat treatment to form an insulating layer, for example.

The metal of the metal alkoxide is, for example, selected from transition metals, lanthanides and main-group elements. Specific examples include barium (Ba), strontium (Sr), titanium (Ti), bismuth (Bi), tantalum (Ta), zirconium (Zr), iron (Fe), nickel (Ni), manganese (Mn), lead (Pb), lanthanum (La), lithium (Li), sodium (Na), potassium (K), rubidium (Rb), cesium (Cs), francium (Fr), beryllium (Be), magnesium (Mg), calcium (Ca), niobium (Nb), thallium (Tl), mercury (Hg), copper (Cu), cobalt (Co), rhodium (Rh), scandium (Sc) and yttrium (Y). The alkoxide of the metal alkoxide includes ones derived from alcohols including methanol, ethanol, propanol, iso-propanol, butanol and iso-butanol; and alkoxy alcohols including methoxyethanol, ethoxyethanol, propoxyethanol, butoxyethanol, pentoxyethanol, heptoxyethanol, methoxypropanol, ethoxypropanol, propoxypropanol, butoxypropanol, pentoxypropanol and heptoxypropanol.

In the invention, when the insulating layer is constituted from the above-mentioned materials, polarization is easy to occur in the insulating layer so that the threshold voltage of the transistor operation can be reduced. Among the above-mentioned materials, in particular when the insulating layer is formed of silicon nitride such as $Si_3N_4$, $Si_xN_y$ or $SiON_X$ (x, y>0), a depletion layer generates more easily so that the threshold voltage of the transistor operation can be further reduced.

For the insulating layer formed from an organic compound, polyimide, polyamide, polyester, polyacrylate, photo-curable resins such as photo-radical polymerization systems and photo-cation polymerization systems; copolymers containing an acrylonitrile component, polyvinylphenol, polyvinylalcohol, novolak resins, cyanoethyl pullulan and the like can be used.

In addition, polymeric materials having high dielectric constant, such as wax, polyethylene, polychloropyrene, polyethylene terephthalate, polyoxymethylene, polyvinyl chloride, poly(vinylidene fluoride), polysulfone, polyimidocyanoethylpullulan, poly(vinylphenol)(PVP), poly(methylmethacrylate)(PMMA), polycarbonate (PC), polystyrene (PS), polyolefin, polyacrylamide, poly(acrylic acid), novolak resin, resole resin, polyimide, polyxylylene and epoxy resin, as well as pullulan and the like can be used.

As the organic compound material and the polymeric material used for the insulating layer, materials having water repellency are particularly preferable. The water repellency of the insulating layer controls the interaction between the insulating layer and the organic semiconductor layer, and the crystallinity of the organic semiconductor layer is increased by using the cohesive property which an organic semiconductor inherently has so that the device performance can be improved. As the examples, poly(p-xylylene) derivatives described in Yasuda et al., Jpn. J. Appl. Phys. Vol. 42 (2003) pp. 6614-6618 and materials disclosed in Janos Veres et al., Chem. Mater., Vol. 16 (2004) pp. 4543-4555 can be mentioned.

When those organic compounds are used as the material for the insulating layer in top gate structures as shown in FIGS. 1 and 4, the insulating layer can be formed with smaller damage given to the organic semiconductor layer, therefore it being effective method.

The insulating layer may be a layer in which a plurality of the above-mentioned inorganic and organic compound materials are mixed or may have a stacked layer structure thereof. In this case, the device performance can be controlled by mixing or stacking a material having high dielectric constant and a material having water repellency, if necessary.

The insulating layer may be an anodic oxide film or contain the anodic oxide film as the component. The anodic oxide film is preferably sealed. The anodic oxide film is formed by a known anodic oxidation method of a metal capable of being anodic oxidized. The metals capable of being anodic oxidized include aluminum and tantalum. The method of anodic oxidization is not particularly limited, and known methods may be used. An oxide film is formed by the anodic oxidation. As an electrolyte used for the anodic oxidation, any electrolyte can be use so long as it can form a porous oxide film. In general, sulfuric acid, phosphoric acid, oxalic acid, chromic acid, boric acid, sulfamic acid and benzenesulfonic acid, and mixed acids of two or more kinds thereof and salts thereof are used. Conditions of the anodic oxidation cannot be necessarily specified because they vary significantly depending upon the kinds of electrolytes used. However, the conditions are typically appropriate that the concentration of the electrolyte is within a range of 1 to 80 mass %, the temperature of the electrolyte within a range of 5 to 70° C., the current density within a range of 0.5 to 60 A/cm$^2$, the voltage within a range of 1 to 100 V, and electrolysis time within a range of 10 seconds to 5 minutes. In the preferred anodic oxidation, an aqueous solution of sulfuric acid, phosphoric acid or boric acid as an electrolyte is used, and direct current electricity is used. However, alternating current can also be used. The concentrations of these acids are preferably 5 to 45 mass %, and electrolysis is preferably carried out at the temperature of the electrolyte of 20 to 50° C. and the current density of 0.5 to 20 A/cm$^2$ for 20 to 250 seconds.

The thickness of the insulating layer has to be appropriately selected because, when it is too small, effective voltage applied to the organic semiconductor becomes large so that the driving voltage and the threshold voltage of the device itself can be reduced while leakage current between the source-gate becomes large. The thickness of the insulating layer is typically 10 nm to 5 μm, preferably 50 nm to 2 μm and more preferably 100 nm to 1 μm.

Any orientation treatment may be applied to between the insulating layer and the organic semiconductor layer. As a preferred treatment, a method of reducing the interaction between the insulating layer and the organic semiconductor layer by imparting water repellency with the surface of the insulating layer or the like and to increase the crystallinity of the organic semiconductor layer. Specifically, a method may be mentioned in which a silane coupling agent such as hexamethyldisilazane, octadecyltrichlorosilane or trichloromethylsilazane; or a self-assembly alignment film material such as an alkanephosphoric acid, an alkanesulfonic acid or an alkanecarboxylic acid is contacted to the surface of the insulating film in the liquid phase or gas phase to form a self-assembly film, followed by moderate drying treatment. Also, a method is preferable in which a film formed of polyimide or the like is allocated on the surface of the insulating film and is subjected to rubbing treatment, as is used for alignment of liquid crystal.

Methods of forming the insulating layer include dry processes such as vapor vacuum deposition, molecular beam epitaxy, ion cluster beam technique, low-energy ion beam technology, ion plating, CVD method, sputtering, and atmospheric pressure plasma disclosed in JP-A-H11-61406, JP-A-H11-133205, JP-A-2000-121804, JP-A-2000-147209 and JP-A-2000-185362; and wet processes, for example, application methods such as spray coating, spin coating, blade coating, dip coating, casting, roll coating, bar-coating and die coating, and patterning methods such as printing and inkjet. These methods can be used depending upon the kind of the material used. As the wet process, a method of application and drying a liquid in which inorganic oxide fine particles are dispersed in any organic solvent or water, if necessary, by using a dispersing aid such as a detergent; and a so-called sol-gel process wherein a solution of an oxide precursor such as an alkoxide form is applied and dried are employed.

The method of fabricating the organic thin film transistor of the invention is not particularly limited, and known methods may be used. However, according to the desired device structure, a sequence of processes for fabricating the device, which includes introduction of a substrate, and formations of a gate electrode, an insulating layer, an organic semiconductor layer, a source electrode and a drain electrode, are preferably carried out without contacting with air at all, because impairment of the device performance caused by moisture, oxygen and the like in air when contacted with air can be prevented. If exposure to air once is unavoidable, the steps after forming an organic semiconductor layer are preferably conducted not in contact with air at all. Just before the formation of the organic semiconductor layer, a surface on which the organic semiconductor layer is stacked (for example, a surface in which a source electrode and a drain electrode are stacked on a portion of an insulating layer) is preferably exposed to ultraviolet ray, ultraviolet ray and ozone, oxygen plasma, argon plasma or the like to clean or activate the surface, followed by stacking of the organic semiconductor layer. On the other hand, some materials for p-type TFT are improved in their performance by contacting with air once and absorbing oxygen or the like. Thus, such materials are in contact with air, if necessary.

Furthermore, for instance, taking effects of oxygen, water and the like contained in air on an organic semiconductor layer into consideration, a gas barrier layer may be formed on a whole or partial surface of the circumference of the organic semiconductor device. As materials for forming the gas barrier layer, ones usually used in this field can be used. Specific examples include polyvinylalcohol, ethylene-vinylalcohol copolymer, polyvinyl chloride, polyvinylidene chloride and poly(chlorotrifluoroethylene). The inorganic substance having insulating property as exemplified in the insulating layer can also be used.

According to the invention, an organic thin film light-emitting transistor can be provided which emits light by using a current flowing between a source electrode and a drain electrode, and in which the light is controlled by applying a voltage to a gate electrode. Namely, the organic thin film transistor can be used as a light emitting device (organic EL). The transistor to control light emission and the light emitting device can be integrated so that the aperture area ratio in a display can be improved and production costs can be reduced by simplifying the production process, whereby it gives great merits for practical uses. When it is used as an organic light emitting transistor, it is necessary to inject holes from one of a source electrode and a drain electrode and electrons from the other. For increasing the light-emitting performance, the following conditions are preferably satisfied.

In the organic thin film light-emitting transistor of the invention, to increase hole-injecting property, at least one of the source electrode and the drain electrode is preferably a hole-injecting electrode. The hole-injecting electrode means an electrode containing a substance having a work function of 4.2 eV or more, The upper limit of the work function of the hole-injecting electrode is 7.0 eV, for example.

Further, to increase electron-injecting property, at least one of the source electrode and the drain electrode is preferably an electron-injecting electrode. The electron-injecting electrode means an electrode containing a substance having a work function of 4.3 eV or less. The lower limit of the work function of the electron-injecting electrode is 1.8 eV, for example.

An organic thin film light-emitting transistor wherein one of these electrodes is the hole-injecting electrode and another electrode is the electron-injecting electrode is more preferable.

To improve hole-injecting property, a hole-injecting layer is preferably provided between at least one of the source electrode and the drain electrode, and the organic semiconductor layer. The material for the hole-injecting layer includes amine-based materials which are used in organic EL devices as hole-injecting material or hole-transporting material.

To improve the electron-injecting property, an electron-injecting layer is preferably provided between at least one of the source electrode and the drain electrode, and the organic semiconductor layer. As in the same as the hole-injecting layer, materials for the electron-injection layer include electron-injecting materials which are used in organic EL devices.

A more preferable organic thin film light-emitting transistor has a hole-injecting layer at one of the electrodes and an electron-injecting layer at another.

Devices using the organic thin film transistor of the invention may be ones using the organic thin film transistor of the invention, and include circuits, personal computers, displays and mobile phone devices.

EXAMPLES

Now, the invention will be explained more detail with reference to examples. Synthesis Example 1 (Synthesis of Compound (A-5))

Compound (A-5) was synthesized as follows. The synthesis process is shown below.

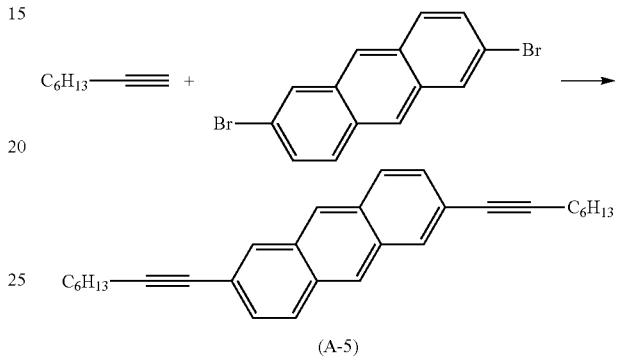

(A-5)

At room temperature, 3.6 g of 2,6-dibromoanthracene, 0.57 g of tetrakis(triphenylphosphine)palladium, 0.20 g of copper iodide (I) were placed, and argon substitution was conducted. To the resultant, 30 ml of triethylamine and 1.1 g of 1-octine were added, and the resulting mixture was subjected to reflux with heating in argon atmosphere for 9 hours. Water and methylene chloride were added to the reaction mixture, an organic layer was separated, followed by drying with anhydrous magnesium sulfate. After concentration under reduced pressure by means of an evaporator, the resulting solid was purified by means of a silica gel column chromatography, followed by purification through sublimation. As a result, 2.7 g of a compound (A-5) was obtained.

It was confirmed that the product was the desired compound by FD-MS (Field Desorption Mass Spectrometry) determination. The determination result by FD-MS is as follows:

FD-MS, calcd for $C_{30}H_{34}$=394, found, m/z=394 (M+, 100)
<FD-MS Determination>
Equipment: HX110 (manufactured by JEOL Ltd.)
Conditions: Acceleration voltage 8 kV
Scan range m/z=50-1500

Example 1

Fabrication of Organic Thin Film Transistor

An organic thin film transistor as shown in FIG. 3 was fabricated in the following procedure. First, a glass substrate was subjected to ultrasonic cleaning with a neutral detergent, pure water, acetone and ethanol each for 30 minutes. Subsequently, gold (Au) was formed into a thin film having a thickness of 40 nm by sputtering to form a gate electrode. Then, the substrate was placed in a film-forming section of a thermal CVD reactor. On the other hand, to an evaporation section of a raw material, 250 mg of poly(p-xylene) derivative [poly(p-xylene) chloride (Parylene)] (Tradename: diX-C, manufactured by Daisan Kasei Co., Ltd.) which was the material for an insulating layer, which was put in a petri dish, was placed. The thermal CVD reactor was vacuated by a vacuum pump to a reduced pressure of 5 Pa. Subsequently, the evaporation section was heated up to a temperature of 180° C., a polymerization section up to a temperature of 680° C., and they were left to stand for 2 hours to form the insulating layer having a thickness of 1 μm on the gate electrode.

Subsequently, Compound (A-2) was dissolved in chloroform to a concentration of 0.5 wt %. The solution was applied on the substrate having the layers up to the insulating layer formed thereon by a spin coater (manufactured by MIKASA CO., LTD.; 1H-D7) to form a film, followed by drying under nitrogen atmosphere at a temperature of 80° C., to form an organic semiconductor layer.

Then, by means of a vacuum vapor deposition apparatus, gold (Au) was deposited thereon through a metal mask into a film having a thickness of 50 nm to provide a source electrode and a drain electrode with a distance (channel length L) of 75 μm therebetween so that they did not contact each other. At this time, the source electrode and the drain electrode were formed such that each width (channel width W) of the electrodes was 5 mm, to obtain an organic thin film transistor.

A gate voltage of −40 V was applied to the gate electrode of the resultant organic thin film transistor, and a voltage was applied to between the source-drain to flow the current. In this case, holes are induced to the channel region (between source-drain) of the organic semiconductor layer and it acts as a p-type transistor. As a result, the on/off ratio of the current between the source-drain electrodes in the saturation current region was $2 \times 10^5$. The field effect mobility p of holes was calculated by the following expression (A) and found to be $1 \times 10^{-2}$ cm$^2$/Vs.

$$I_D = (W/2L) \cdot C\mu \cdot (V_G - V_T)^2 \quad (A)$$

In the expression, $I_D$ denotes a source-drain current, W a channel width, L a channel length, C an electrical capacity per unit area of the gate insulating layer, $V_t$ a gate threshold voltage, and $V_g$ a gate voltage.

Examples 2 and 3

Fabrication of Organic Thin Film Transistor

An organic thin film transistor was fabricated in the same manner as in Example 1 except that Compound (A-3) and Compound (A-5) was used in place of Compound (A-2) as a material for the organic semiconductor layer. In the same manner as in Example 1, the resultant organic thin film semiconductor was p-type driven at a gate voltage $V_G$ of −40 V. The on/off ratio of the current between the source-drain electrodes was measured, and the field effect mobility μ of holes was calculated. The results are shown in Table 1.

Example 4

Fabrication of Organic Thin Film Transistor

In the same manner as in Example 1, cleaning of a substrate, formation of a gate electrode and formation of an insulating layer were carried out. Next, the substrate was placed in a vacuum deposition apparatus (manufactured by ULVAC, EX-400), and Compound (A-5) was deposited on the insulating layer at a deposition rate of 0.05 m/s to form a film having a thickness of 50 nm as an organic semiconductor layer. Then, by means of a vacuum vapor deposition apparatus, gold (Au) was deposited thereon through a metal mask into a film having a thickness of 50 nm to provide a source electrode and a drain electrode which did not contact each other, whereby an organic thin film transistor was fabricated.

In the same manner as in Example 1, the resultant organic thin film semiconductor was p-type driven at a gate voltage $V_G$ of −40 V. The on/off ratio of the current between the source-drain electrodes was measured, and the field effect mobility μ of holes was calculated. The results are shown in Table 1.

TABLE 1

| | Compound for organic semi-conductor layer | Transistor type | Field effect mobility (cm$^2$/Vs) | On/off ratio |
|---|---|---|---|---|
| Ex. 1 | A-2 | p-type | $2 \times 10^{-1}$ | $2 \times 10^5$ |
| Ex. 2 | A-3 | p-type | $1 \times 10^{-1}$ | $3 \times 10^5$ |
| Ex. 3 | A-5 | p-type | $1 \times 10^{-1}$ | $2 \times 10^5$ |
| Ex. 4 | A-5 | p-type | $5 \times 10^{-1}$ | $5 \times 10^5$ |

INDUSTRIAL APPLICABILITY

As explained in detail above, by using the compound having the specific structure and high electron mobility as the material for an organic semiconductor layer, the organic thin film transistor of the invention has a rapid response speed (driving speed) and a large on/off ratio, is a high performance transistor, and can also be used as an organic thin film light-emitting transistor capable of emitting light.

The documents described in the specification are incorporated herein by reference in its entirety.

The invention claimed is:

1. A compound for an organic thin film transistor having a structure shown by the following formula (1):

$$X^1\text{-L-Ar-L-}X^2 \quad (1)$$

wherein

L is —C≡C—, or —CH═CH— in a trans configuration, $X^1$ and $X^2$ are independently an alkyl group having 2 to 30 carbon atoms or a haloalkyl group having 1 to 30 carbon atoms, and Ar is a substituted or unsubstituted aromatic hydrocarbon group having 14 to 60 ring carbon atoms which is a condensed ring of three or more rings, or a substituted or unsubstituted aromatic heterocyclic group having 11 to 60 ring atoms which is a condensed ring of three or more rings, and wherein the substituents of the aromatic hydrocarbon group and the aromatic heterocyclic group are selected from the group consisting of a halogen atom, a cyano group, a haloalkyl group having 1 to 30 carbon atoms, a haloalkoxy group having 1 to 30 carbon atoms and a haloalkysulfonyl group having 1 to 30 carbon atoms.

2. The compound for an organic thin film transistor according to claim 1, wherein the bonding positions between $X^1$ and L, between $X^2$ and L, and between Ar and L are configured such that the pi-conjugated structure formed by $X^1$-L-Ar-L-$X^2$ has the maximum conjugation length.

3. The compound for an organic thin film transistor according to claim 1, wherein Ar has a symmetric structure.

4. The compound for an organic thin film transistor according to claim 1, wherein Ar has a substituent, and the substituent is a halogen atom or a cyano group.

5. The compound for an organic thin film transistor according to claim 1, wherein $X^1$ and $X^2$ are the same.

6. An organic thin film transistor, which comprises three terminals of a gate electrode, a source electrode and a drain electrode, an insulating layer, and an organic semiconductor layer, and wherein a source-drain current is controllable by the application of a voltage to the gate electrode, and wherein the organic semiconductor layer comprises the compound according to claim 1.

7. The organic thin film transistor according to claim 6, which is capable of emitting light by the electric current between the source-drain electrodes, and is capable of controlling the light emission by the application of a voltage to the gate electrode.

8. The organic thin film transistor according to claim 7, wherein one of the source and drain electrodes is formed of a substance having a work function of 4.2 eV or higher, and another thereof is formed of a substance having a work function of 4.3 eV or lower.

9. The organic thin film transistor according to claim 6, which has a buffer layer between the source and drain electrodes and the organic semiconductor layer.

10. A device, comprising the organic thin film transistor according to claim 6 and at least one other component of said device.

11. A compound having a structure shown by the following formula (2):

wherein
L is —C≡C—, or —CH=CH— in a trans configuration,
$X^1$ and $X^2$ are independently an alkyl group having 2 to 30 carbon atoms or a haloalkyl group having 1 to 30 carbon atoms, and
Ar' is one of the following structures:

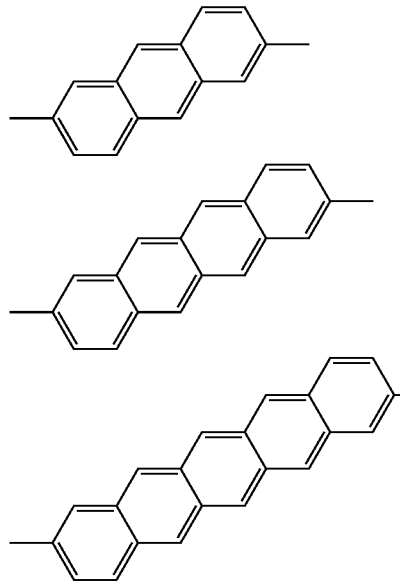

12. An organic thin film transistor, which comprises three terminals of a gate electrode, a source electrode and a drain electrode, an insulating layer, and an organic semiconductor layer, and wherein a source-drain current is controllable by the application of a voltage to the gate electrode, and wherein the organic semiconductor layer comprises the compound according to claim 11.

13. The organic thin film transistor according to claim 12, which is capable of emitting light by the electric current between the source-drain electrodes, and is capable of controlling the light emission by the application of a voltage to the gate electrode.

14. The organic thin film transistor according to claim 13, wherein one of the source and drain electrodes is formed of a substance having a work function of 4.2 eV or higher, and another thereof is formed of a substance having a work function of 4.3 eV or lower.

15. The organic thin film transistor according to claim 12, which has a buffer layer between the source and drain electrodes and the organic semiconductor layer.

16. A device, comprising the organic thin film transistor according to claim 12 and at least one other component of said device.

17. A compound for an organic thin film transistor having a structure shown by the following formula (1):

wherein
L is —C≡C—, or —CH=CH— in a trans configuration,
$X^1$ and $X^2$ are independently an alkyl group having 2 to 30 carbon atoms or a haloalkyl group having 1 to 30 carbon atoms, and
Ar is one of the following structures:

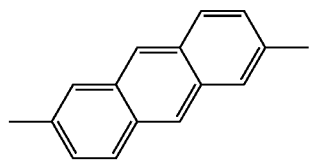

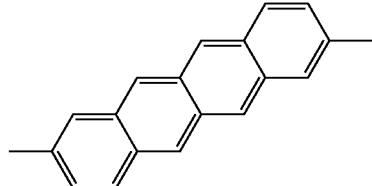

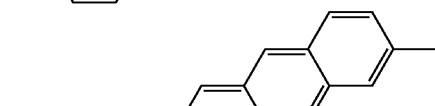

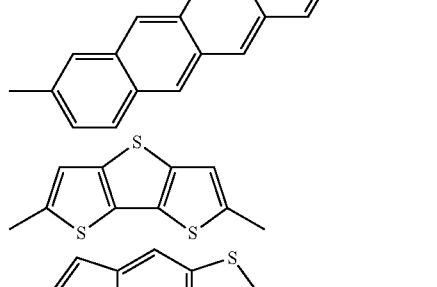

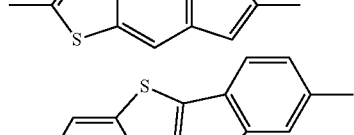

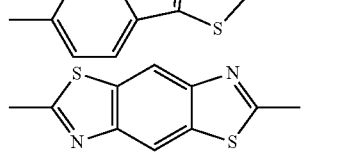

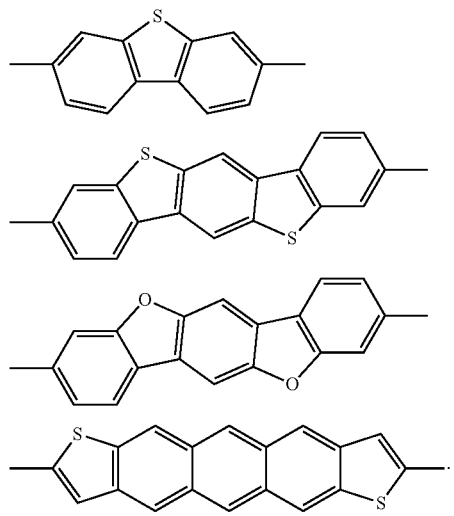

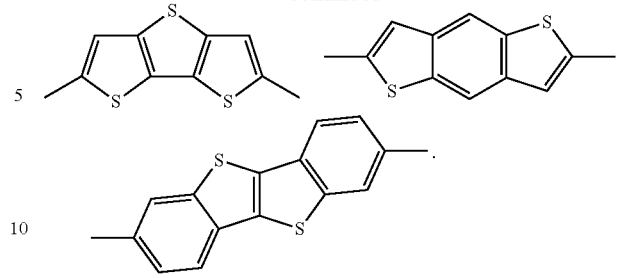

18. The compound for an organic thin film transistor according to claim 17, wherein
Ar is one of the following structures:

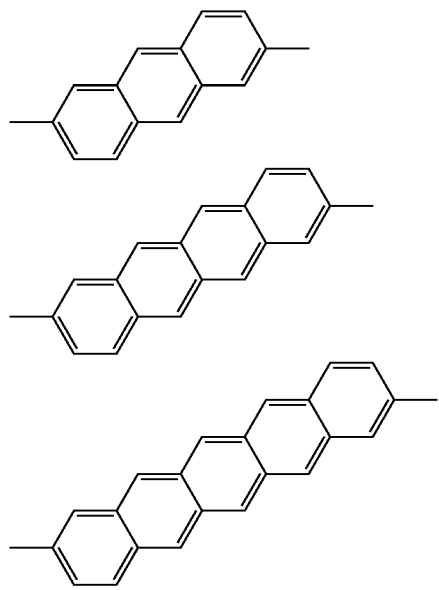

19. An organic thin film transistor, which comprises three terminals of a gate electrode, a source electrode and a drain electrode, an insulating layer, and an organic semiconductor layer, and wherein a source-drain current is controllable by the application of a voltage to the gate electrode, and wherein the organic semiconductor layer comprises the compound according to claim 17.

20. A device, comprising the organic thin film transistor according to claim 19 and at least one other component of said device.

21. The compound for an organic thin film transistor according to claim 17, which is one of the following compounds

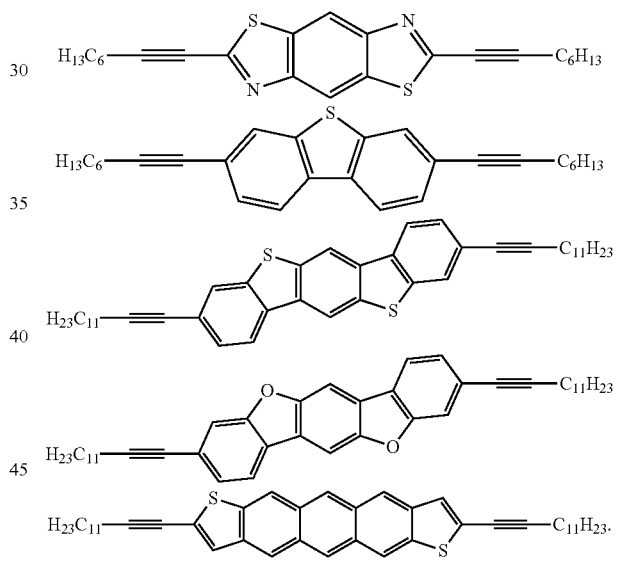

* * * * *